US010060895B2

(12) United States Patent
Bauer et al.

(10) Patent No.: US 10,060,895 B2
(45) Date of Patent: Aug. 28, 2018

(54) DEVICES AND METHODS FOR IDENTIFYING A BIOLOGICAL OR CHEMICAL RESIDUE IN AN LIQUID SAMPLE

(71) Applicants: Alan Joseph Bauer, Jerusalem (IL); Nethanel Raisch, Psagot (IL); Charles H. Panzarella, Shaker Heights, OH (US)

(72) Inventors: Alan Joseph Bauer, Jerusalem (IL); Nethanel Raisch, Psagot (IL); Charles H. Panzarella, Shaker Heights, OH (US)

(73) Assignee: Light of Detection, Ltd., Jerusalem (IL)

( * ) Notice: Subject to any disclaimer, the term of this patent is extended or adjusted under 35 U.S.C. 154(b) by 246 days.

(21) Appl. No.: 14/979,373

(22) Filed: Dec. 27, 2015

(65) Prior Publication Data

US 2017/0184562 A1  Jun. 29, 2017

(51) Int. Cl.
*G01N 27/02* (2006.01)
*G01N 27/00* (2006.01)
*G01N 33/18* (2006.01)
*G01N 27/60* (2006.01)

(52) U.S. Cl.
CPC ......... *G01N 33/1826* (2013.01); *G01N 27/02* (2013.01); *G01N 27/023* (2013.01); *G01N 27/60* (2013.01)

(58) Field of Classification Search
CPC .............................. G01N 27/02; G01N 27/023
See application file for complete search history.

(56) References Cited

U.S. PATENT DOCUMENTS

| | | | | |
|---|---|---|---|---|
| 2007/0181424 A1* | 8/2007 | Frey | ................... | G01N 33/5438 204/403.01 |
| 2011/0068807 A1* | 3/2011 | Kesil | ................... | G01N 27/023 324/633 |
| 2014/0116158 A1* | 5/2014 | Minteer | ................... | B01L 3/502 73/863.01 |
| 2015/0064723 A1* | 3/2015 | Mutharasan | ..... | G01N 33/54373 435/7.23 |
| 2015/0301031 A1* | 10/2015 | Zin | ................... | G01N 33/48792 436/164 |

OTHER PUBLICATIONS

Ravelo, B., et al. "Demonstration of the triboelectricity effect by the flow of liquid water in the insulating pipe." Journal of Electrostatics 69.6 (2011): 473-478.*

* cited by examiner

*Primary Examiner* — Lisa Caputo
*Assistant Examiner* — Herbert K Roberts

(57) ABSTRACT

The invention discloses methods and devices for rapidly detecting a biological and/or chemical residue in a liquid sample. In some embodiments of the instant invention, a single antenna is generally employed in proximity to an aqueous solution in a disposable cup, with electrical outputs being recorded by an electrical metering device in communication with the single antenna. Commercial plastic cups may be used for detection of electric fields related to cleanliness of water samples. General and specific target detection may be performed with various embodiments of the instant invention.

8 Claims, 19 Drawing Sheets

DEVICES AND METHODS FOR IDENTIFYING A BIOLOGICAL OR CHEMICAL RESIDUE IN AN LIQUID SAMPLE

FIELD AND BACKGROUND OF THE INVENTION

The instant invention, in some embodiments thereof, is directed to the detection and/or identification of chemical or biological contaminants in a liquid sample. This application claims priority of U.S. Provisional Patent Application 62/255,426 filed 14 Nov. 2015 & U.S. Provisional Patent Application 62/260,540 filed 29 Nov. 2015 of common inventorship, and said applications are incorporated in their entirety.

Inventors note that they tried to file this application on 24-27 Dec. 2015, but due to the power outage of 22 December at the USPTO, they were unable to file online via EFS-Web. Also, this application is being filed outside of the US and does not allow for delivery via USPS mail.

SUMMARY OF THE INVENTION

It is a purpose of the present invention, in some embodiments, to provide methods and devices for detecting the presence of at least one predetermined material or material class in a liquid sample through the action of generating electric field via the motion of a liquid against a hydrophobic surface.

The invention includes a device for identifying the presence of a predetermined material or class of materials in a liquid sample, including: a hydrophobic receiving element adapted to receive a liquid sample; an electronic circuit adapted to identify an electric field, wherein the circuit is adapted to be placed in proximity to the receiving element; an outcome indicator in electrical communication with the electronic circuit and adapted to convey to a user a presence and/or strength of an electrical field associated with the receiving element; and, a source of electrical energy adapted to provide electrical energy to the electronic circuit and the indicator.

In one aspect of the device, the receiving element is realized as a plastic cup, drinking glass, disposable shot glass, mug, bottle, pipe, sink, faucet, tubing, container or other element adapted to receive a liquid.

In another aspect of the device, the proximity is realized as a distance of zero to 20 centimeters.

In another aspect of the device, the predetermined material or class of materials is realized as chemical entities, biological residues, organic compounds, pesticides, proteins, viruses, parasites or bacteria.

In another aspect of the device, the electronic circuit includes a FET element.

In another aspect of the device, there is additionally a processor element adapted to receive data from the electronic circuit and control the outcome indicator.

In another aspect of the device, there is additionally a GPS element for identifying location of the electronic circuit at a time of measurement of the electric field.

In another aspect of the device, there is additionally a communication element adapted to send data from the processor element to a remote computing device.

In another aspect of the device, the remote computing device is realized as a smartphone, wearable device or mobile electronic device.

The invention includes a method for determining the composition of a liquid sample, including the following: providing an electrical circuit that includes an electric field detector; providing a hydrophobic receiving element adapted to receive a portion of a liquid sample; placing a liquid sample into the hydrophobic receiving element; swirling the liquid sample in the hydrophobic receiving element for a predetermined amount of time or for a predetermined number of revolutions; placing the electric field detector in proximity to the hydrophobic receiving element; measuring presence and/or strength of an electrical field in proximity to the hydrophobic receiving element; determining a presence or absence of a predetermined material or plurality of materials in the liquid sample as a function of strength of the electric field; and, indicating to a user the presence or absence of the predetermined material or plurality of materials in the liquid sample.

In one aspect of the method, the predetermined material or materials are selected from bacteria, viruses, heavy metals, proteins, nucleic acids, organic compounds, pesticides, inorganic ions, salts, or any combination thereof.

In another aspect of the method, the receiving element is realized as a disposable plastic cup made from polypropylene, polystyrene, or polyethylene terephthalate.

In another aspect of the method, the receiving element is realized as a plastic cup, glass, mug, bottle, pipe, tubing, faucet, sink, container or other element adapted to receive a liquid.

In another aspect of the method, the step of displaying is performed by one or a plurality of LED elements and/or via an audio element.

In another aspect of the method, the swirling is performed manually for three seconds or for three revolutions of liquid in the hydrophobic receiving element.

In another aspect of the method, the electrical circuit includes a source of electrical energy.

In another aspect of the method, the electrical circuit includes a communication element adapted for transmittal of data from a component of the circuit to an external device.

In another aspect of the method, the proximity is realized as being a distance of zero to 20 centimeters.

The invention additionally includes a device for identifying electric fields associated with hydrophobic surfaces, including: an electronic circuit adapted to identify electric fields associated with a plastic cup, wherein an antenna associated with said electronic circuit is adapted to be in non-contact proximity to said plastic cup; a processing unit adapted to process electric field strength data received from the electronic circuit; an outcome indicator in electrical communication with the processor unit and adapted to convey to a user an electric field strength; a memory element adapted to store electrical field strength data; a communication element adapted to transmit the electric field strength data to an external device; and, a source of electrical energy adapted to provide electrical energy to the electronic circuit, the processing unit and the outcome indicator.

In one aspect of the device, the communication element includes a wireless transmission component.

In another aspect of the device, the wireless transmission component is selected from WiFi, Bluetooth, IR, or NFC.

In another aspect of the device, the non-contact proximity is realized as between 0.5 and 20 centimeters.

The invention includes a method for determining the composition of a liquid sample, including the following: providing an electrical circuit that includes an electric field detector; providing a hydrophobic receiving element adapted to receive a portion of a liquid sample; placing a liquid sample into the hydrophobic receiving element; placing the electric field detector in proximity to the hydrophobic receiving element; measuring presence and/or strength of an electrical field in proximity to the hydrophobic receiving element; determining a presence or absence of a predetermined material or plurality of materials in the liquid sample as a function of strength of the electric field; and, indicating to a user the presence or absence of the predetermined material or plurality of materials in the liquid sample.

In one aspect of the method, a quantity of material in the liquid sample is determined by a height at which an LED associated with the electric field detector remains lit.

The invention includes a method for detecting chemical or biological residues in a liquid sample, including: providing a receiving element having a first electronegative property; placing a liquid sample into the receiving element, wherein the liquid sample has a second electronegative property; causing the liquid sample to move relative to the receiving element; measuring electric fields associated with the receiving element; and, determining a presence of chemical or biological residues in the liquid sample according to a strength and/or location of the electric fields.

The invention includes a method for determining the composition of a liquid sample, including the following: providing an electrical circuit that includes an electric field detector; providing a hydrophobic receiving element adapted to receive a portion of a liquid sample; placing a liquid sample into the hydrophobic receiving element; swirling the liquid sample in the hydrophobic receiving element; placing the electric field detector in proximity to the hydrophobic receiving element; measuring presence and/or strength of an electrical field in proximity to the hydrophobic receiving element; determining a presence or absence of a predetermined material or plurality of materials in the liquid sample as a function of strength of the electric field; and, indicating to a user the presence or absence of the predetermined material or plurality of materials in the liquid sample.

Unless otherwise defined, all technical and/or scientific terms used herein may have the same general meanings as commonly understood by a practitioner of ordinary skill in the art to which the invention pertains. The instant invention does not send or provide electrical, wave, or other energy to a sample; rather, devices of the instant invention receive de novo signals without any application of power or voltage to a sample.

"Static electricity" and "electric field" may have their generally understood meanings as related to the electrical arts. It is understood that contact of different material may lead to charge transfer, wherein one material becomes more negatively charged while the other material, including liquids, may become more positively charged, as per triboelectric theory. Unbalanced charges, both positive and negative, generally have associated electric fields. Field strength and directionality may vary according to specific conditions of the material, the net charge, and the environment in which the charge is located. A general assumption may be that increasing unbalanced (net) charge may have a larger electric field associated with it. Detection of electric fields may be a means of detecting unbalanced charges and/or static charges.

"Hydrophobic" may have its generally understood meaning as applied to the chemical arts. A "receiving element" may generally be described as an element adapted to receive a liquid sample. A cup, mug, glass, pipes, faucets, tubing, and the like are non-limiting examples of receiving elements adapted to receive a liquid sample and in some cases to hold said liquid sample for a period of time. An "aqueous solution" may generally be any water-based solution that may possibly include salts or other materials. It is understood that the instant invention may be equally applied to any and all types of liquids and any and all types of contaminants or residues may potentially be identified or quantified. In some applications, a receiving element may be hydrophilic.

An "electronic circuit" or "electric circuit" may generally include a plurality of elements such as resistors, FET's and other electronic elements. One or more antennae may be employed in electric field or electric potential detection. An electronic circuit may be adapted to detect and/or measure electric fields and/or electric potentials associated with a surface. An "outcome indicator" may generally refer to one or a plurality of elements adapted to relate a presence or absence of electric fields to a user. A plurality of colored LED's, a programmable screen or variable audio signals are non-limiting examples of outcome indicators for some embodiments of the instant invention. An "electric field" may include all forms of fields generated by or associated with charged moieties, electrons, or static charges. A "smartphone" includes any power driven device including machines, specific glasses, water bars, filtration machines or part of the above.

An analyte, residue, material, group of materials or target may generally be a material that is the subject of detection and/or quantification. Bacteria and viruses as well as heavy metals, organic compounds, nerve agents, proteins, peptides and pesticides are non-limiting examples of potential residues for the instant invention. "Proximity" for the instant invention may generally refer to a distance between a receiving element and an electronic circuit or an antenna associated with an electronic circuit of zero (full contact) to 50 centimeters. A "communication element" may generally refer to an element adapted to communicate between an electronic circuit or associated controller and a remote device such as a computer, smartphone, handheld computing device, laptop, wearable devices, glasses or the like. Communication may involve wired or wireless means. Wireless means may include WiFi, IR, NFC, Bluetooth or other methods for wirelessly transferring data. An "electric field detector" may generally refer to an electronic element adapted to identify and/or measure electric field strength. Certain FET devices as well as other electronic elements are adapted to have a change in current as a function of being present in or near an exogenous electric field. A device may include one or a plurality of FET or similar elements to allow for a wide range of electric field detection.

"Swirling" may refer to any means of moving a liquid relative to a receiving element. Swirling, shaking, vortexing, vibrating, passing, agitating, moving, spilling, mixing, adding, and dripping are non-limiting examples of swirling as intended in the instant invention. While swirling may be performed for a predetermined amount of time (measured in seconds generally) or number of revolutions, in some embodiments, a user may swirl a receiving element with liquid sample for no particular period of time or number of revolutions and then make a measurement thereafter. Period of time and number of revolutions may not have to be fixed for the instant invention. The same is true for force of swirling and/or mixing. A period of time may be a minimum, for example, "at least one second" or the like.

The instant invention generally does not apply any electrical signal or energy to a sample. Rather electric charges and/or their associated electric fields may be identified in their association with a cup or the like and optionally quantified, wherein presence, absence, or size of an electric field may give information on the contents of a liquid sample in said cup or the like. It is understood that anywhere measurement of electric field strength is mentioned, one could as easily measure electric potential. The two are treated as the same with respect to measurements for the instant invention.

Electrical energy may be provided by battery, solar power, human motion, a wall power source, generator, disposable battery, reusable battery, rechargeable battery, multiple batteries or power sources, or other appropriate energy sources. In some embodiments, no electrical energy may be required.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It is noted that similar elements in various drawings may have the same number, advanced by the appropriate multiple of 100. In the drawings.

DESCRIPTION OF SPECIFIC EMBODIMENTS
OF THE INVENTION

The present invention, in some embodiments thereof, relates to methods and devices for detecting the presence of chemical and/or biological residues in a liquid by virtue of measuring a presence and/or strength of an electric field of a container in which the liquid is located.

While it is well-known that hydrophobic liquids can impart static electricity on plastic pipes, there is little known about water doing the same. Water is a highly polar solvent and is generally not considered in triboelectric tables. Yet, swirling water in a disposable plastic cup made of typical polymers such as polypropylene, polystyrene, PETE, styrene, PET or the like can leave a charge on the plastic. If bacteria, proteins, heavy metals, certain heavy metal salts, or other biological residues are present in water, the amount of charge generated and/or left on the plastic can be significantly reduced or brought to zero over seconds to minutes. The net effect is to have a differential electric field associated with a disposable cup, bottle or the like as a function of how clean a water sample is.

The instant invention, in some embodiments, is founded on electrical effects generally generated by moving a liquid sample relative to a hydrophobic container. Previously filed applications (U.S. patent application Ser. No. 13/975,340; PCT/IL2015/050721) discussed the movement of water in a disposable pipette tip or similar liquid delivery element. The instant invention has removed the need for a flowing sample or a disposable pipette tip. Measurements may be made in situ by doing no more than optionally swirling a water sample in a plastic cup and then identifying electric fields in proximity to the plastic cup prior to drinking from the same plastic cup.

Figure 1:
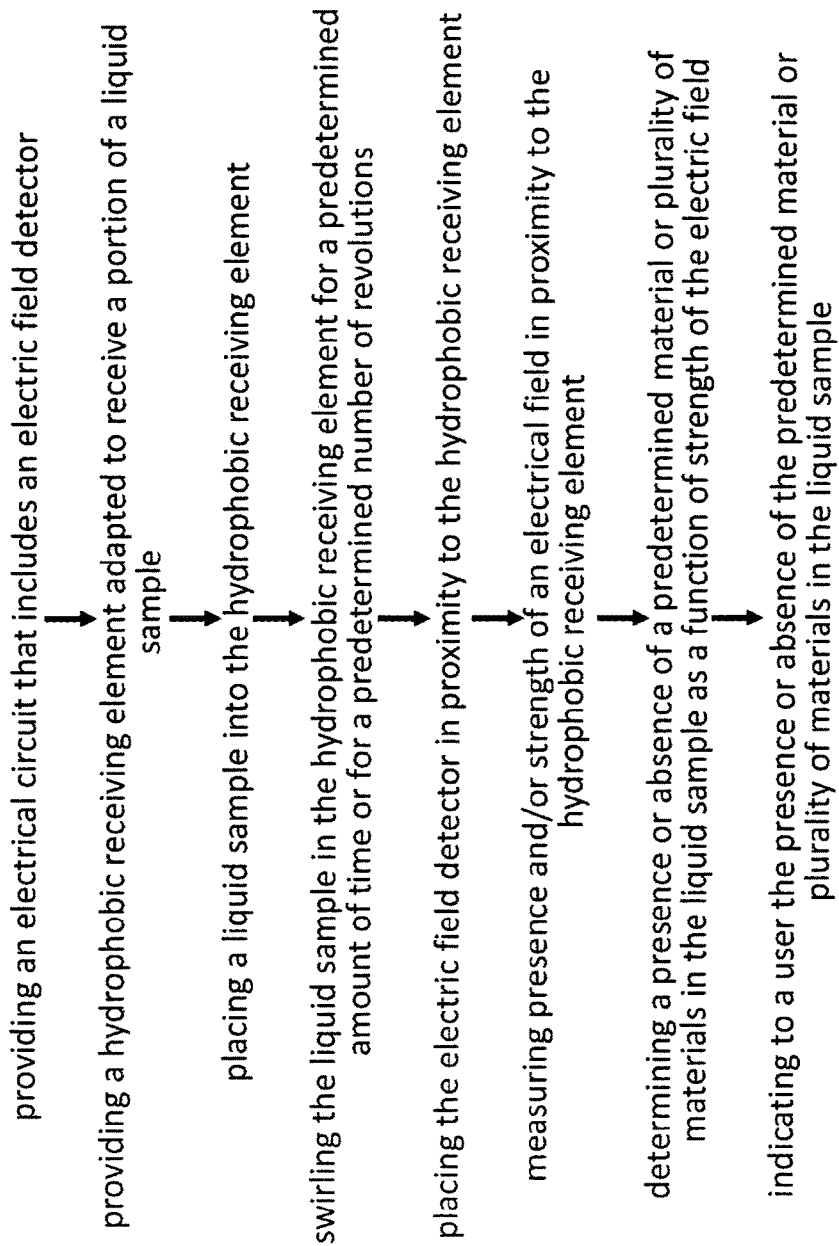
FIG. 1 shows a flowchart of a method of the invention.

In the embodiments and examples below, the sensor is described in greater detail. It is understood that other embodiments not formally described are possible without deviating from the spirit and intent of the instant invention.
First Embodiment Attention is turned to FIG. 1 which shows a flowchart for a method of the instant invention. The invention includes a method for determining the composition of a liquid sample, including the following: providing an electrical circuit that includes an electric field detector; providing a hydrophobic receiving element adapted to receive a portion of a liquid sample; placing a liquid sample into the hydrophobic receiving element; swirling the sample liquid in the hydrophobic receiving element for a predetermined amount of time or for a predetermined number of revolutions; placing the electric field detector in proximity to the hydrophobic receiving element; measuring presence and/or strength of an electrical field in proximity to the hydrophobic receiving element; determining a presence or absence of a predetermined material or plurality of materials in the liquid sample as a function of strength of the electric field; and, indicating to a user the presence or absence of the predetermined material or plurality of materials in the liquid sample.

In one aspect of the method, the predetermined material or materials are selected from bacteria, viruses, heavy metals, proteins, nucleic acids, organic compounds, pesticides, inorganic ions, salts, oils, other liquids or any combination thereof. In another aspect of the method, the receiving element is realized as a disposable plastic cup made from polypropylene, polystyrene, or polyethylene terephthalate. In another aspect of the method, the receiving element is realized as a plastic cup, glass, mug, bottle, pipe, tubing, faucet, sink, container or other element adopted to receive a liquid. In another aspect of the method, the step of displaying is performed by one or a plurality of LED elements and/or via an audio element. In another aspect of the method, the swirling is performed manually for three seconds or for three revolutions of liquid in the hydrophobic receiving element. In another aspect of the method, the electrical circuit includes a source of electrical energy. In another aspect of the method, the electrical circuit includes a communication element adapted for transmittal of data from a component of the circuit to an external device. In another aspect of the method, the proximity is realized as being a distance of zero to 20 centimeters.

The electronic circuit minimally includes components adapted to detect the presence of electric fields generally associated with static charges as well as components that allow a user to know of the presence and/or field strength of such fields. Electroscopes or inexpensive static electricity detectors are non-limiting examples of components of an electronic circuit that allows for detection of electric fields associated with static charges, said static charges generally associated with a hydrophobic receiving element. The electronic circuit may include other elements such as a LED or plurality of LED's or audio features that serve to provide information to a user as to presence and/or strength of electric fields and by extension quality data regarding the liquid sample analyzed.

A hydrophobic receiving element such as a polypropylene disposable cup is selected as water, in being swirled or otherwise moved relative to the receiving element, causes a transfer of electrons from water to the receiving element. Hydrophilic glasses and the like may be used, but their effect is less pronounced. Swirling of water in a plastic cup or the like leads to generation of static electricity on the plastic cup. The components of clean drinking water such as salt, bicarbonate and magnesium sulfate, do not readily absorb or interact with the generated static charge. The result is that static charge remains high and the electronic circuit may easily detect it. Contaminants such as bacteria, viruses, proteins, peptides, heavy metals, organic materials, pesticides, and the like tend to either reduce electron transfer between liquid and plastic and/or absorb or otherwise interact with the electrons to effectively reduce the amount of static charge present. The electric field detector records a smaller field strength and may, via an appropriate indicator element such as said LED or plurality of LED's, display that the lower field strength is indicative of contaminants being present in a liquid sample.

Measuring presence and/or strength of electric field associated with the hydrophobic receiving element may be performed by one of many possible means. The receiving element may be brought into proximity (generally 0-20 centimeters) of the electronic circuit or vice versa. The cup may be placed at a predetermined distance from the electronic circuit and then the electronic circuit can be allowed to receive electrical energy so as to allow for a reading or identification of an electric field.

It is understood that one does not need to swirl liquid sample in the receiving element, but by doing so, more charge is generated and a greater differential field strength may be measured between clean samples and those with bacteria present in the few cfu's/mL or proteins present at fg/mL or the like. In some embodiments, in place of swirling, a hydrophobic receiving element may be contacted or rubbed against another object to generate static electricity. Metallic surfaces are preferred for such contact or rubbing prior to bringing the receiving element towards the electronic circuit or vice versa. It is understood that one may ground, zero, or otherwise reset an electronic circuit or a component thereof before or between measurements.

Second Embodiment

The invention includes a device for identifying the presence of a predetermined material or class of materials in a liquid sample, including: a hydrophobic receiving element adapted to receive a liquid sample; an electronic circuit adapted to identify an electric field, wherein the circuit is adapted to be placed in proximity to the receiving element; an outcome indicator in electrical communication with the electronic circuit and adapted to convey to a user a presence and/or strength of an electrical field associated with the receiving element; and, a source of electrical energy adapted to provide electrical energy to the electronic circuit and the indicator.

In one aspect of the device, the receiving element is realized as a plastic cup, drinking glass, disposable shot glass, mug, bottle, pipe, sink, faucet, tubing, container or other element adapted to receive a liquid. In another aspect of the device, the proximity is realized as a distance of zero to 20 centimeters. In another aspect of the device, the predetermined material or class of materials is realized as chemical entities, biological residues, organic compounds, pesticides, proteins, viruses, parasites or bacteria. In another aspect of the device, the electronic circuit includes a FET element. In another aspect of the device, there is additionally a processor element adapted to receive data from the electronic circuit and control the outcome indicator. In another aspect of the device, there is additionally a GPS element for identifying location of the electronic circuit at a time of measurement of the electric field. In another aspect of the device, there is additionally a communication element adapted to send data from the processor element to a remote computing device. In another aspect of the device, the remote computing device is realized as a smartphone, wearable device or mobile electronic device.

Figure 2:
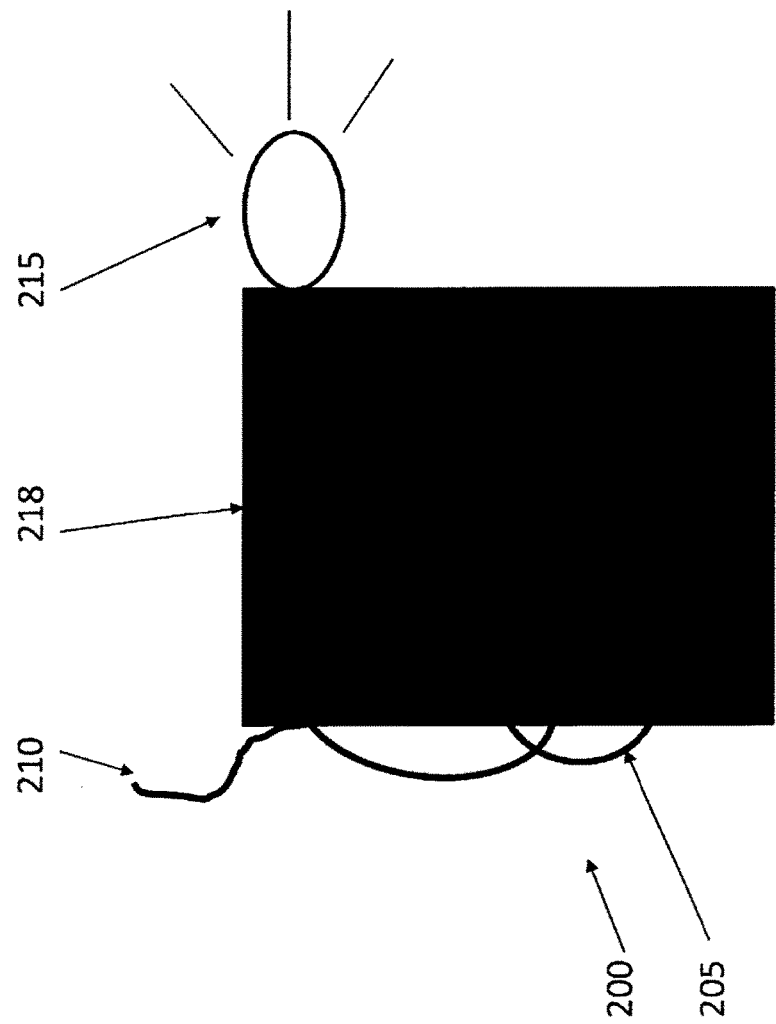
FIGS. 2-4 show photographs of a device according to an embodiment of the instant invention.
Figure 3:
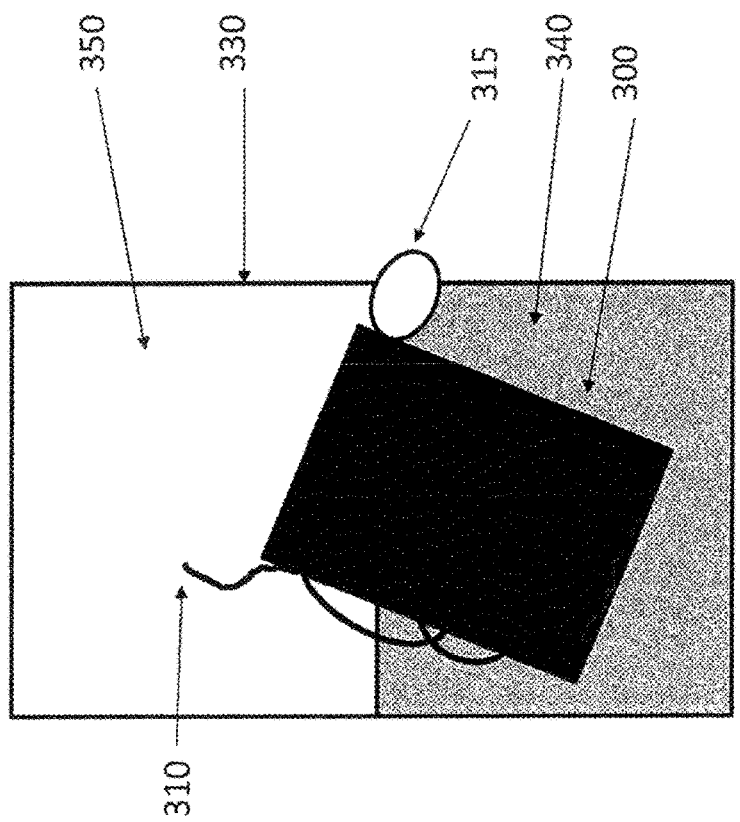
Figure 4:
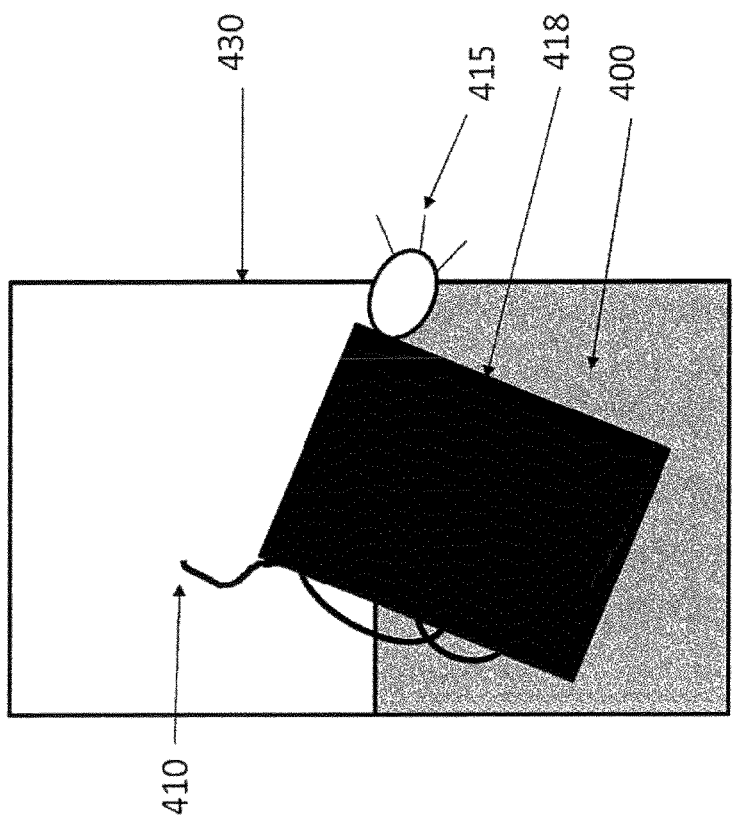

Attention is turned to FIG. 2 which shows a photographic view of a detection device as per the instant embodiment of the invention. A water monitoring device 200 includes a 3V watch battery 205, an antenna 210, a display LED 215 and an electronic circuit 218 adapted to detect electric fields. The LED 215 is shown lit. Attention is turned to FIG. 3 which shows the water monitoring device 300 next to a polypropylene disposable cup 330 that includes mineral water 340. Spinning of the cup 330 (not shown) followed by placement of the antenna 310 five centimeters from the cup leads to the LED 315 being turned off by the action of the electric fields associated with the dry region 350 of the cup 330. FIG. 4 shows a similar cup 430 that includes 10 ng/mL of Lysozyme (Sigma, L6876). Contact of the antenna 415 of the monitoring device 400 leads to no change in the lit LED 415. As the protein serves to wipe out electric fields on the cup 430, there is no electric field interfering with electronic circuit 418.

Third Embodiment

The invention additionally includes a device for identifying electric fields associated with hydrophobic surfaces, including: an electronic circuit adapted to identify electric fields associated with a plastic cup, wherein an antenna associated with said electronic circuit is adapted to be in non-contact proximity to said plastic cup; a processing unit adapted to process electric field strength data received from the electronic circuit; an outcome indicator in electrical communication with the processor unit and adapted to convey to a user an electric field strength; a memory element adapted to store electrical field strength data; a communication element adapted to transmit the electric field strength data to an external device; and, a source of electrical energy adapted to provide electrical energy to the electronic circuit, the processing unit and the outcome indicator.

In one aspect of the device, the communication element includes a wireless transmission component. In another aspect of the device, the wireless transmission component is selected from WiFi, Bluetooth, IR, or NFC.

Figure 5:
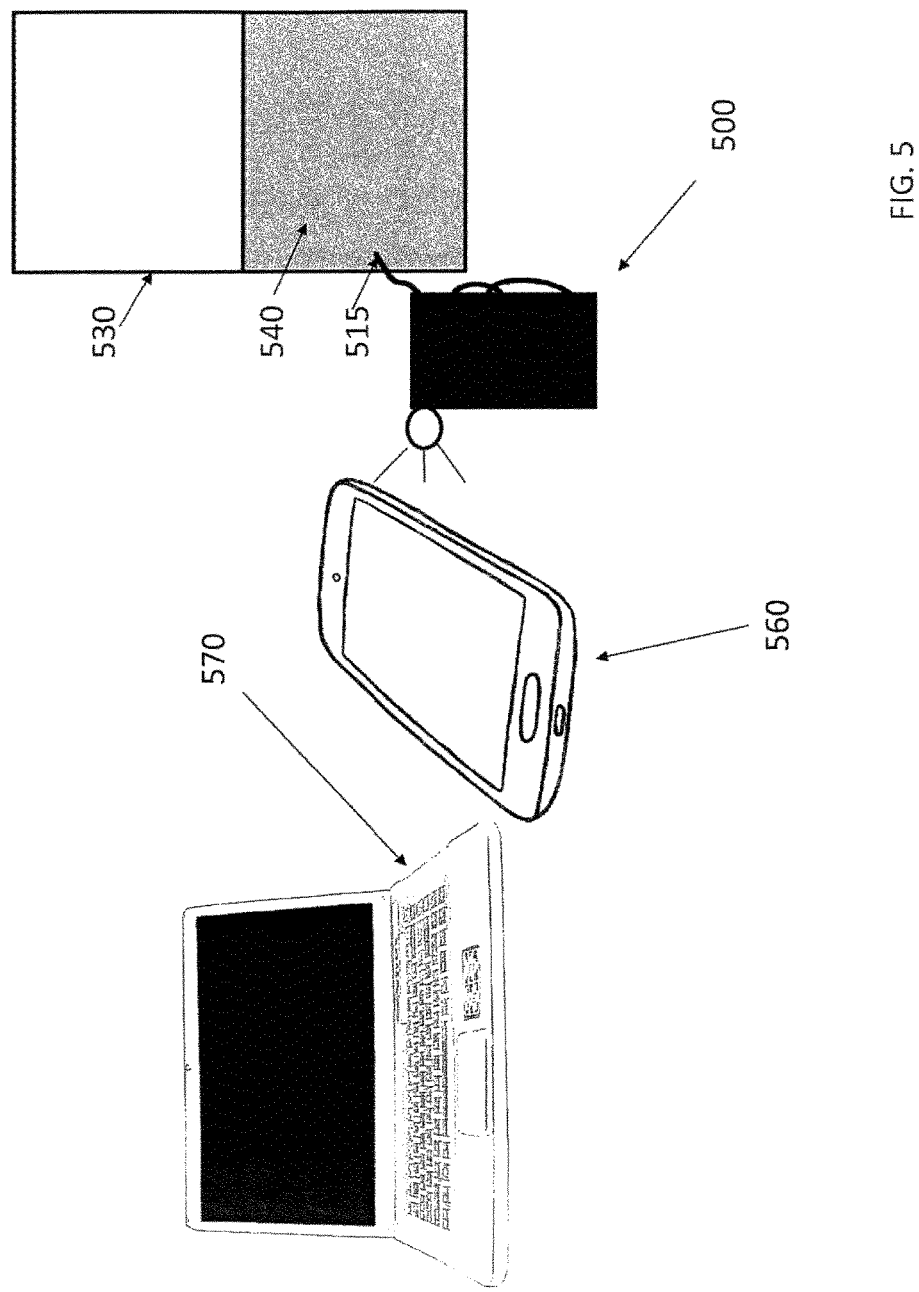
FIG. 5 shows a photograph of a device according to another embodiment of the invention.

The wireless transmission component allows for transfer of data from a detection unit to a smartphone with appropriate application and/or other computer device or mobile computing device. Data collected can be gathered into databases for analyses as well as for regional and global analysis of water quality. FIG. 5 shows an arrangement wherein a cup 530 is used to get data on water 540 with protein (note LED lit) in the cup 530, the data being sent from the detection device 500 to a smartphone 560 via NFC and then via WiFi to a laptop computer 570 where a database is stored and local water quality maps are generated. The antenna 515 in some embodiments may contact the cup 530, while in most applications, there is no contact between them.

Other sensor features that optionally may be included in a sensor device include GPS for identification of location where testing took place, a gyro to know absolute sensor orientation, thermometer, camera, proximity detector, laser, magnetometer, compass, solar power cell, clock, internal memory, USB or other jacks, a screen-optionally touchscreen—and buttons with indicator lights. It is understood that a sensor could be realized as a plurality of sensors and could be involved in multiple tests simultaneously or in series. It is understood that a cup 530 could be patterned with antibodies, receptors, or other binding agents that show some level of binding to a specific analyte or class of analytes in order to allow for specific identification of a liquid contaminant.

Figure 6C:
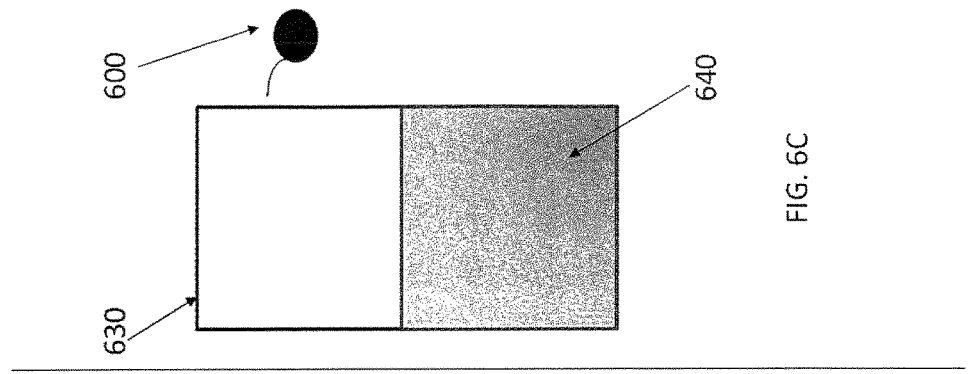
FIGS. 6A-6C show schematic views of relations between a sensor device and a plastic disposable cup during measurement.
Figure 6B:
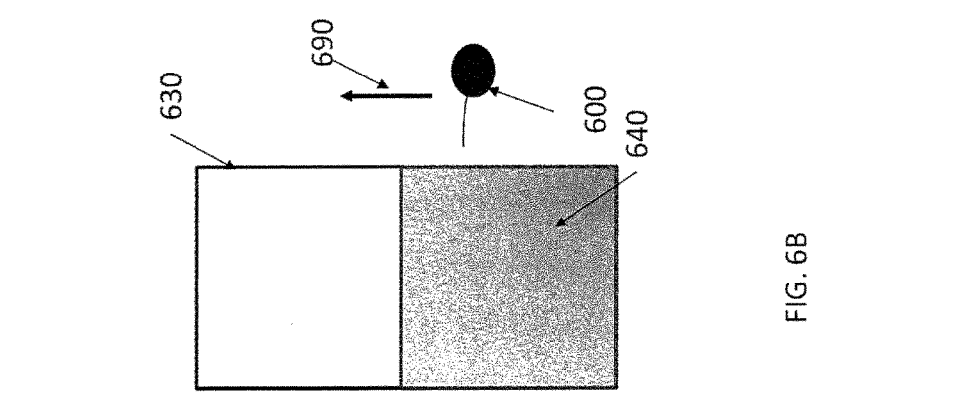
Figure 6A:
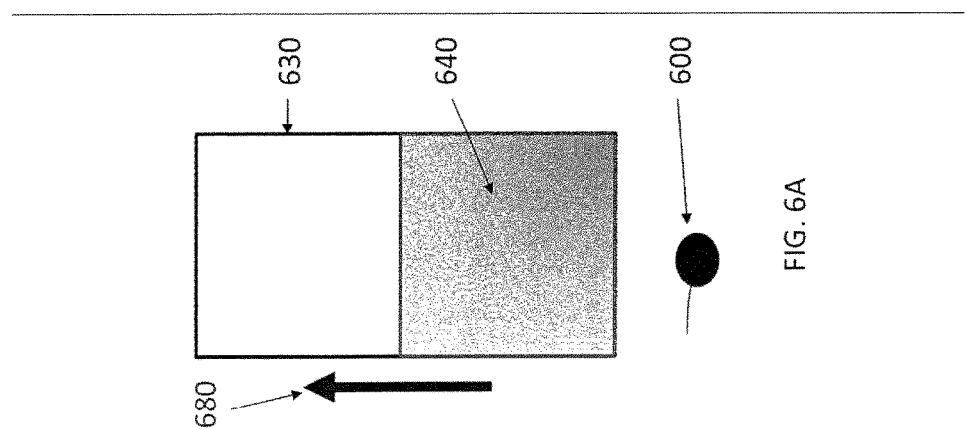

Measurements with the device may be made both in static and movement-based modes. FIGS. 6A-6C show various non-limiting arrangements between an electronic detection circuit and a cup with water. FIG. 6A shows a cup 630 with a liquid sample 640 and a sensor unit 600 placed underneath the cup 630. Measurement may involve moving 680 the cup relative to the sensor unit 600 and then obtaining a reading in the sensor unit 600 as to electric field presence and associated electric field strength, from which one may deduce if the liquid sample was clean or had a contaminant present. FIG. 6B shows a cup 630 with liquid sample 640 and a sensor unit 600 being brought 690 up a side of the cup 630, with measurement being made either continuously or at times during the movement of the sensor unit 600. FIG. 6C shows a static measurement in which a sensor unit 600 is placed at a certain height over the liquid sample 640 in a cup 630 and a measurement is made. Strong electric fields suggest, for example, clean water, while reduced or absent electric fields suggests a contamination of biological or chemical nature, where the contamination reduces static electricity on the cup 630.

It has been discovered that as the sensor unit 600 moves up parallel with the cup 630, the LED (not shown) stays lit the more concentrated a contaminant is present. For example, 1 microgram/milliliter of protein in a mineral water sample will leave the LED on from the bottom to the top of the cup 630. If, on the other hand, the concentration of protein is only 1 femtogram/milliliter, the LED stays lit only a few centimeters above the waterline. This difference in behavior may allow for quantifying amounts of residues present in liquid samples. A similar behavior has been seen in distance between sensor unit 600 and cup 630 when measured above the waterline.

Fourth Embodiment

The invention includes a device for identifying the presence of a chemical or biological residue in a liquid sample, including: a hydrophobic receiving element adapted to receive and hold a liquid sample; an electronic circuit adapted to identify electric charge, wherein the circuit is adapted to be brought into non-contact proximity to the receiving element; a smartphone or mobile electronic device adapted to be in electrical communication with the electronic circuit; an outcome indicator associated with the smartphone or mobile electronic device adapted to convey to a user the presence and strength of static electricity associated with the receiving element; and, a source of electrical energy adapted to provide electrical energy to the electronic circuit and the indicator.

In one aspect of the device, the receiving element is realized as a plastic cup, glass, mug, bottle, container or other element adopted to receive and hold a liquid.

Figure 7C:
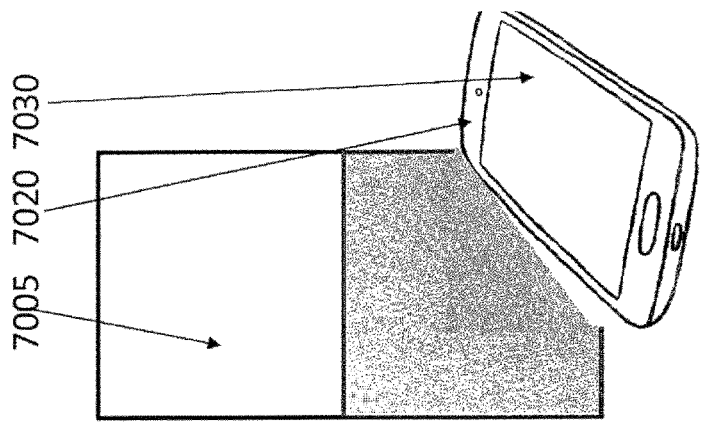
FIGS. 7A-7C show a smartphone with an associated electrostatic field detector being moved relative to a fixed PET cup.
Figure 7B:
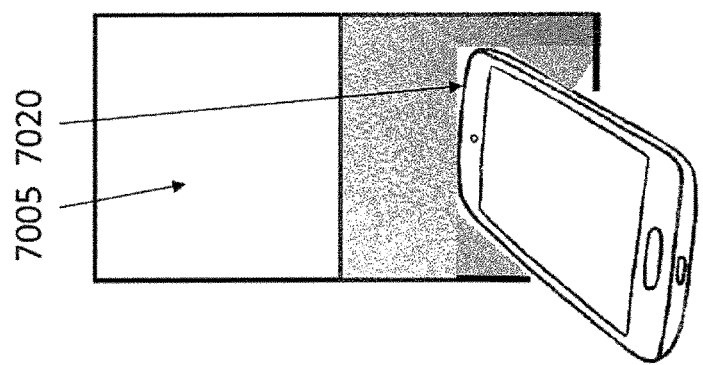
Figure 7A:
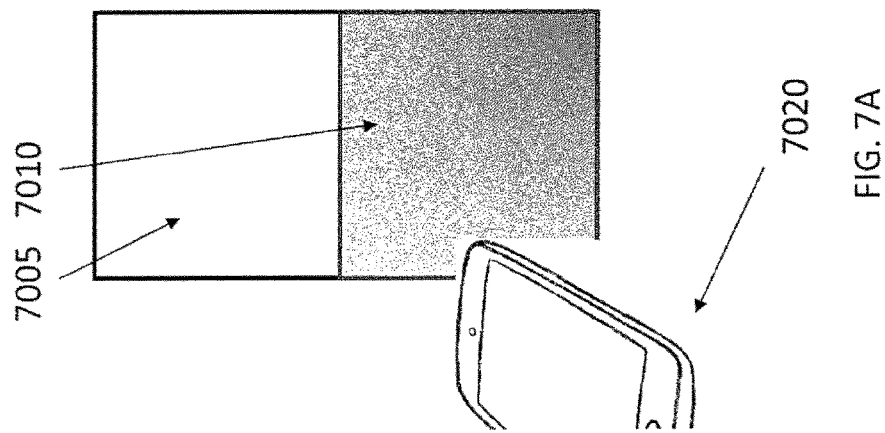

Attention is turned to FIG. 7A. Shown is a PET cup 7005 that includes a water sample 7010 of Neviot (Israel) mineral water. A Samsung Galaxy 4S Mini smartphone 7020 is placed to the left of the cup 7005 and an electrode adapted to register electrical charge (not visible in this view) is adapted to face the cup 7005. FIG. 7B shows the phone 7020 with the electrode passing by the cup 7005 in non-contact proximity at a distance between cup 7005 and phone 7020 of 1 centimeter. Distance between phone 7020 and cup 7005 is generally between 0.1 and 20 centimeters for non-contact proximity. FIG. 7C shows the phone 7020 after it has passed the cup 7005. The cup 7005 was swirled for 3 seconds prior to passage of the phone 7020 in front of a side of the cup 7005. One pass was used, though one may do more than one pass. The touchscreen 7030 of the phone 7005 is adapted to show results for measurements via an appropriate application.

Figure 8:
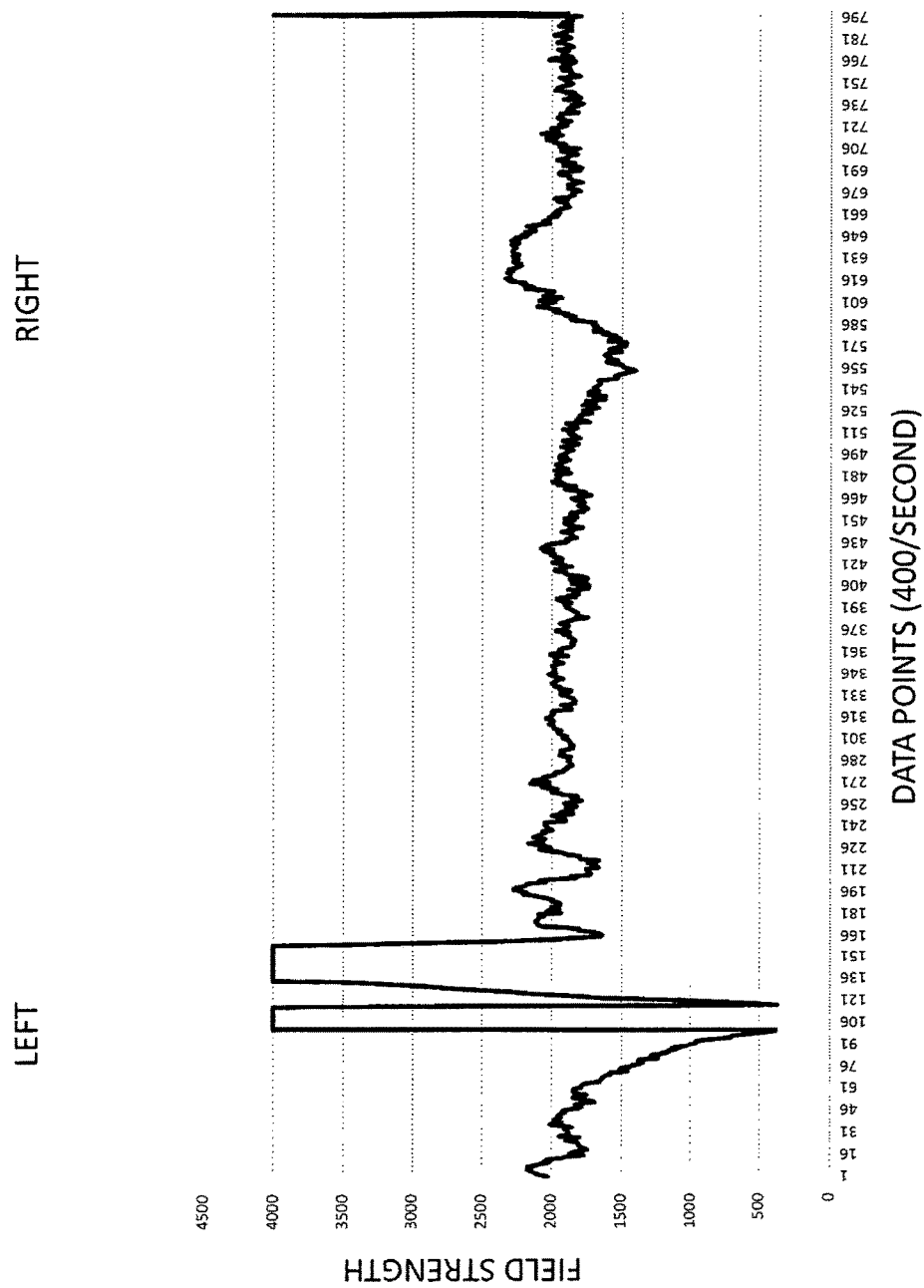
FIG. 8 shows graphs of results for a prototype based on an embodiment of the invention.

FIG. 8 shows results for a prototype system (not shown) based on this instant embodiment. The large peak on the left represents the prototype passing a PET cup when only water is present. The lower output on the right of the graph shows the results when water in a PET cup is spiked with E. coli. There was no contact between the prototype and the cup as the prototype electrode passed 1 centimeter from the PET cups, and there was no signal propagated by the prototype; the prototype only receives signal but does not send any signal whatsoever into liquid sample or elsewhere.

Fifth Embodiment

Figure 9:
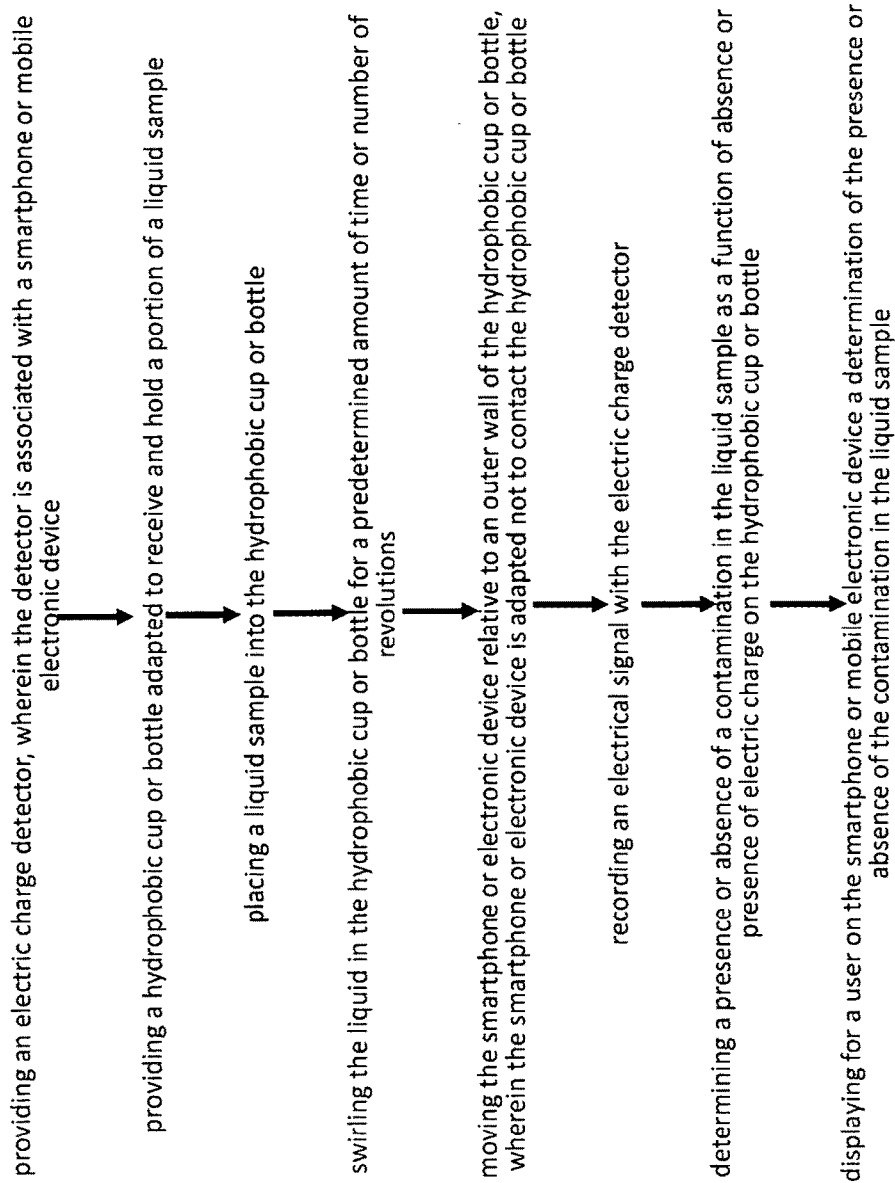
FIG. 9 shows a flowchart of an alternative method of the instant invention.

Attention is turned to FIG. 9 which shows a flowchart for an alternative method of the invention. The invention also includes a method for determining the quality of a liquid sample, including the following: providing an electric charge detector, wherein the detector is associated with a smartphone or mobile electronic device; providing a hydrophobic cup or bottle adapted to receive and hold a portion of a liquid sample; placing a liquid sample into the hydrophobic cup or bottle; swirling the liquid in the hydrophobic cup or bottle for a predetermined amount of time or number of revolutions; moving the smartphone or electronic device relative to an outer wall of the hydrophobic cup or bottle, wherein the smartphone or electronic device is adapted not to contact the hydrophobic cup or bottle; recording an electrical signal with the electric charge detector; determining a presence or absence of a contamination in the liquid sample as a function of absence or presence of electric charge on the hydrophobic cup or bottle; and, displaying for a user on the smartphone or mobile electronic device a determination of the presence or absence of the contamination in the liquid sample.

In one aspect of the method, the contamination is biological. In another aspect of the method, the cup or bottle is made primarily from a polymeric material. In another aspect of the method, the polymeric material is selected from polypropylene, polystyrene, or polyethylene terephthalate.

In another aspect of the method, the moving is accomplished by passing the smartphone or mobile electronic device past the cup or bottle. In another aspect of the method, the moving is accomplished by vibrating the smartphone or mobile electronic device in non-contact proximity to the cup or bottle.

An electric charge detector may be any device or element adapted to detect, sense or measure a charge or the presence of static electricity. Non-limiting examples of cups or bottles for the instant embodiment include PET, polypropylene and polystyrene cups and bottles. Liquid is generally placed in ⅓ of a cup or bottle so as to allow for cup swirling without liquid exiting the cup or bottle. Swirling is a general term and may include shaking, moving, vibrating, rocking or any other means of moving a liquid in a cup or bottle relative to the inner side of said cup or bottle. A smartphone may include a dedicated charge detector or may have one associated via a connector or wireless interaction. Moving the smartphone or mobile electronic device may be performed by any means, including but not limited to manual passing, vibrating, pushing, or swiping. It is understood that one may alternatively or additionally move the cup or bottle relative to the smartphone or mobile electronic device. Additionally, one may move the smartphone or mobile electronic device as well as the cup or bottle during a measurement. The electrical signal may generally be related to the amount of charge associated with the cup or bottle. Determination of presence or absence of contamination is made by evaluating the amount of electric field associated with the cup or bottle. A large amount of charge/associated field generally may mean that the water sample is clean of bacteria, proteins, viruses, organic wastes, or heavy metals that interact with electric fields. A reduced amount of charge may generally imply that the water is contaminated with one or more of the same. Displaying may generally be performed directly on a touchscreen associated with the smartphone or mobile electronic device. Data may optionally be stored and/or transferred via wireless means to a storage site in the cloud or other predetermined location.

Sixth Embodiment

Figure 10:
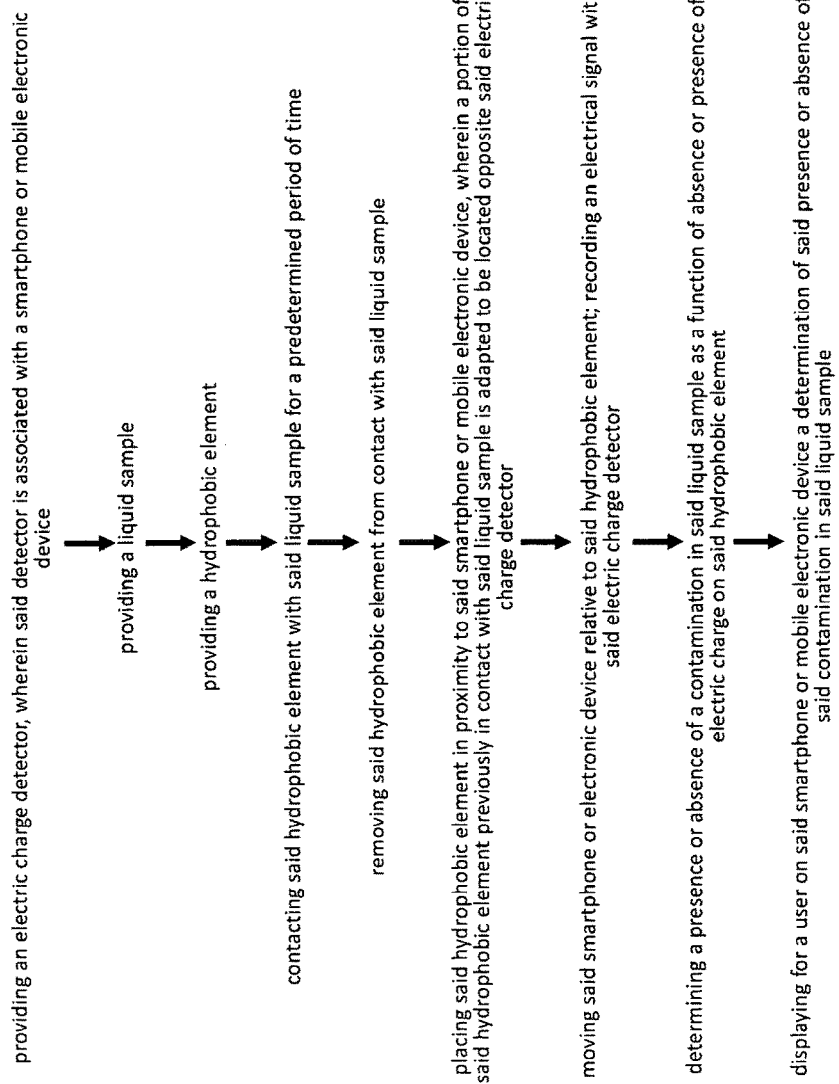
FIG. 10 shows a flowchart of an alternative method of the instant invention.

Attention is turned to FIG. 10 which shows a flowchart for a method of the invention. The invention provides for a method for determining the quality of a liquid sample, including the following: providing an electric charge detector, wherein said detector is associated with a smartphone or mobile electronic device; providing a liquid sample; providing a hydrophobic element; contacting said hydrophobic element with said liquid sample for a predetermined period of time; removing said hydrophobic element from contact with said liquid sample; placing said hydrophobic element in proximity to said smartphone or mobile electronic device, wherein a portion of said hydrophobic element previously in contact with said liquid sample is adapted to be located opposite said electric charge detector; moving said smartphone or electronic device relative to said hydrophobic element; recording an electrical signal with said electric charge detector; determining a presence or absence of a contamination in said liquid sample as a function of absence or presence of electric charge on said hydrophobic element; and, displaying for a user on said smartphone or mobile electronic device a determination of said presence or absence of said contamination in said liquid sample.

In one aspect of the method, the hydrophobic element is realized as a drinking straw. In another aspect of the method, the hydrophobic element is realized as a strip of polymeric material. In another aspect of the method, there is an additional step of moving said hydrophobic element relative to said liquid sample prior to said removing. In another aspect of the method, the predetermined period of time is selected from 1 to 10 seconds. In one embodiment of the invention, there may be an additional step of introducing air into a straw, pipe, tube, tubing, or the like to aid in measurement.

Figure 11:
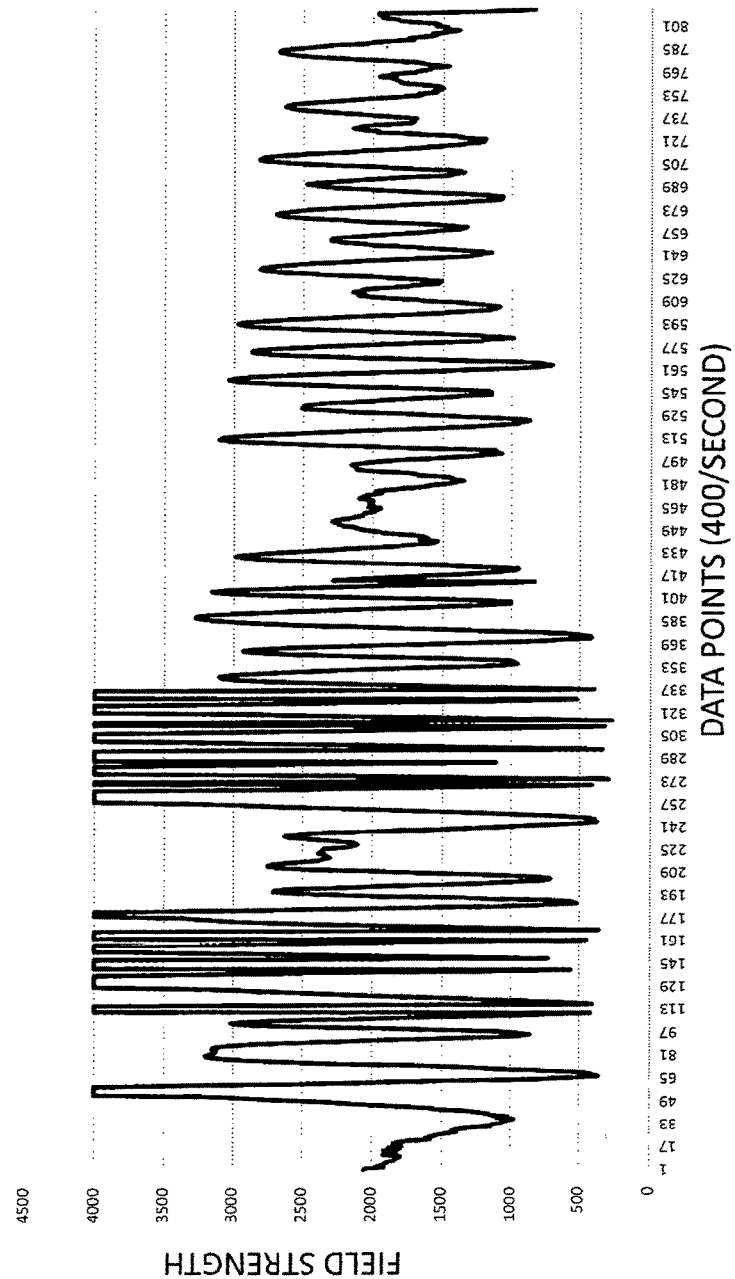
FIG. 11 shows results for an experiment in which plastic drinking straws served as hydrophobic elements.

FIG. 11 shows results for an experiment in which plastic (polypropylene) straws were placed in separate samples of water (LEFT) and water with *E. coli* (RIGHT) at approximately 1,000 cfu's per milliliter. The straws were placed in the liquid samples, moved around in the sample for 3 seconds and then placed in front of an electric field detector. The straws were constantly moved left and right in front of the detector during four seconds of measurements each; it is understood that one could move the detector relative to the straws or other hydrophobic elements, such as strips of polyethylene or other appropriate polymeric material. The lower amplitudes associated with *E. coli* sample relative to clean tap water would alert a user as to the presence of a contamination in his/her water sample.

Seventh Embodiment

Figure 12:
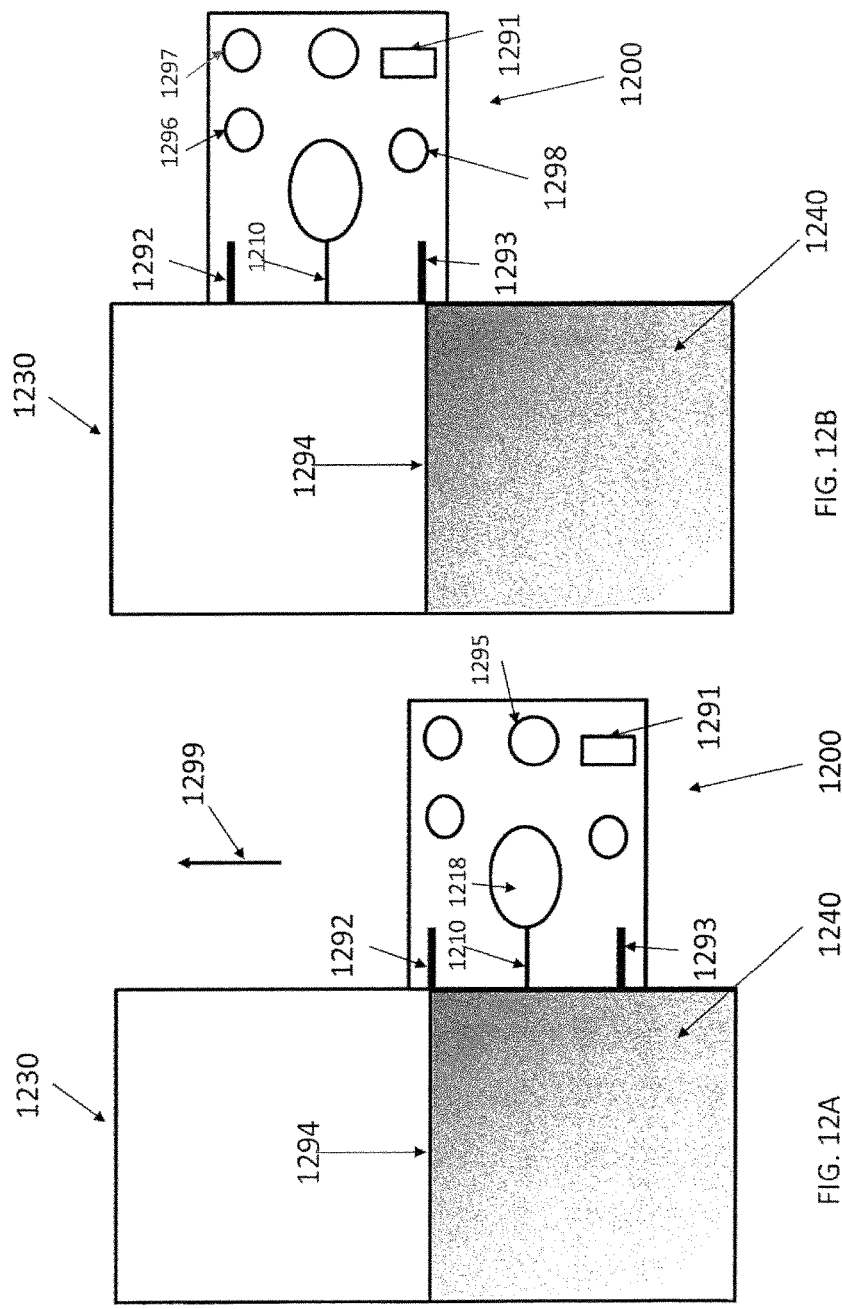
FIGS. 12A-12B show schematic views of an embodiment of the instant invention.

Attention is now turned to FIG. 12A which shows an embodiment of the instant invention. A liquid quality detector 1200 includes a static electricity detector 1218 that includes an antenna 1210. The detector 1200 includes an accelerometer 1291 as well as a first position line 1292 and a second position line 1293. A cup 1230 includes an aqueous sample 1240. The first position line 1292 is lined up with the waterline 1294 in the cup 1230. The liquid quality detector 1200 is activated. A light 1295 shows that the detector 1200 is working. A measurement of electrostatic charge (and associated electric field and/or potential) on the cup 1230 is performed. As the water neutralizes static electricity in the cup 1230 where the aqueous sample 1240 is present, the detector should read no charge. The detector 1200 is moved 1299 up the cup 1230. Attention is turned to FIG. 12B which shows a continuation of the instant measurement. The detector 1200 is slid up the side of the cup 1230 until the second position line 1293 is located at the waterline 1294. The accelerometer 1291 confirms the direction and distance of movement, as the distance between first position line 1292 and second position line 1293 is known. A time restraint may be placed on a measurement. A second measurement is made of static electricity associated with the cup 1230 at a position above the waterline 1294, where antenna 1210 is located. If static electricity is present, a green light 1296 is lit to suggest that no biological or chemical residues are present in the aqueous sample 1240. If static electricity is absent or significantly below a predetermined level, then a red light 1297 will warn a user that a water sample may be contaminated. An additional light 1298 may warn a user that there was an error in the measurement: initial reading showed static electricity or that the detector 1200 was not moved properly, etc. and that a new reading is required. The detector 1200 may contact the cup 1230 or may be up to 20 centimeters away from the cup 1230 during measurement. Battery, on/off switch, memory, clock and other features are not shown so as to allow for easier understanding of the invention. Two or more measurements may be performed in this and any other embodiment of the instant invention.

Figure 13:
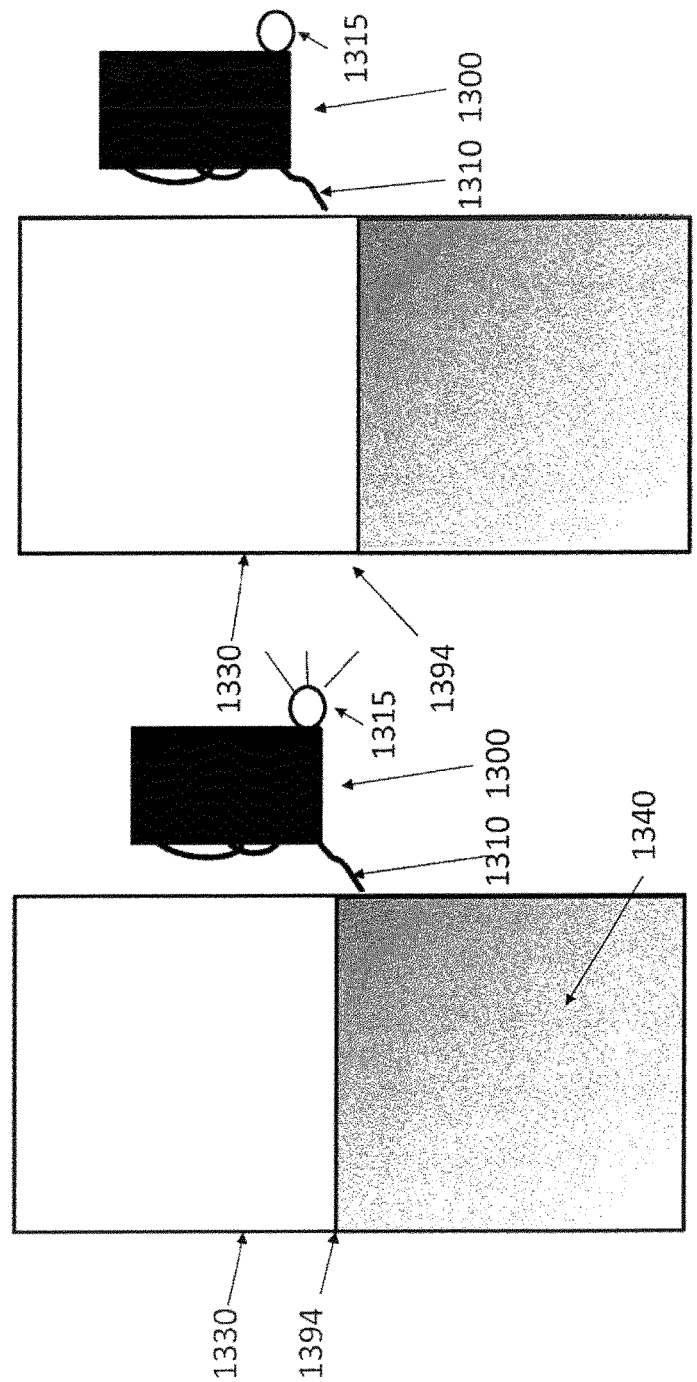
FIGS. 13A-13B show photographs related to the instant embodiment.

Attention is turned to FIG. 13A which shows a cup 1330 with tap water 1340 after swirling of the water 1340 in the cup. A liquid quality detector 1300 with electric field antenna 1310 was placed below the waterline 1394 and a measurement was made. The lit LED 1315 means that the detector 1300 is working as no electric fields are present where water 1340 is present in the cup 1330. In FIG. 13B, the detector 1300 has been moved above the waterline 1394 and another measurement was made. The LED 1315 was off due to the presence of static electricity on the cup 1330 above the waterline 1394. The detector includes an electronic element whose ability to pass current is adversely affected by the presence of nearby electric fields. Certain commercial FET's have been described as having this feature, as described in previously-identified US Provisional Patent Applications.

Figure 14:
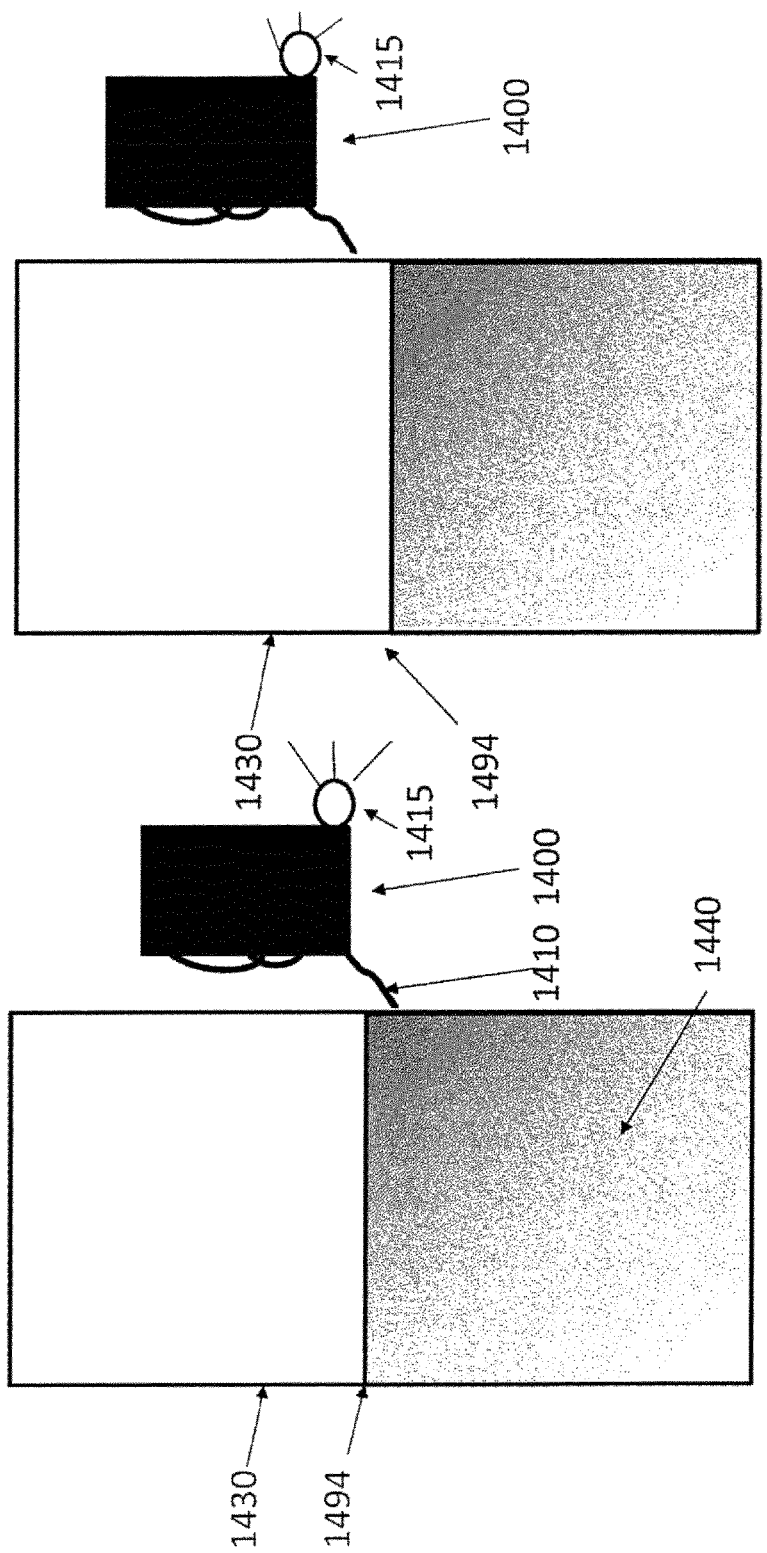
FIGS. 14A-14B show additional photographs related to the instant embodiment.

Attention is turned to FIG. 14A which shows a cup 1430 with tap water 1440 with lysozyme (protein) at 1 ng/mL after swirling of the water 1440 in the cup. A liquid quality detector 1400 with electric field sensitive antenna 1410 was placed below the waterline 1494 and a measurement was made. The lit LED 1415 means that the detector 1400 is working as no electric fields are present where water 1440 is present in the cup 1430. In FIG. 14B, the detector 1400 has been moved above the waterline 1494 and another measurement was made. The LED 1415 was on due to the lack of static electricity on the cup 1330 above the waterline 1394 due to protein presence in the water 1440. Current flows freely to the LED 1415 which is lit.

Eighth Embodiment

Figure 15:
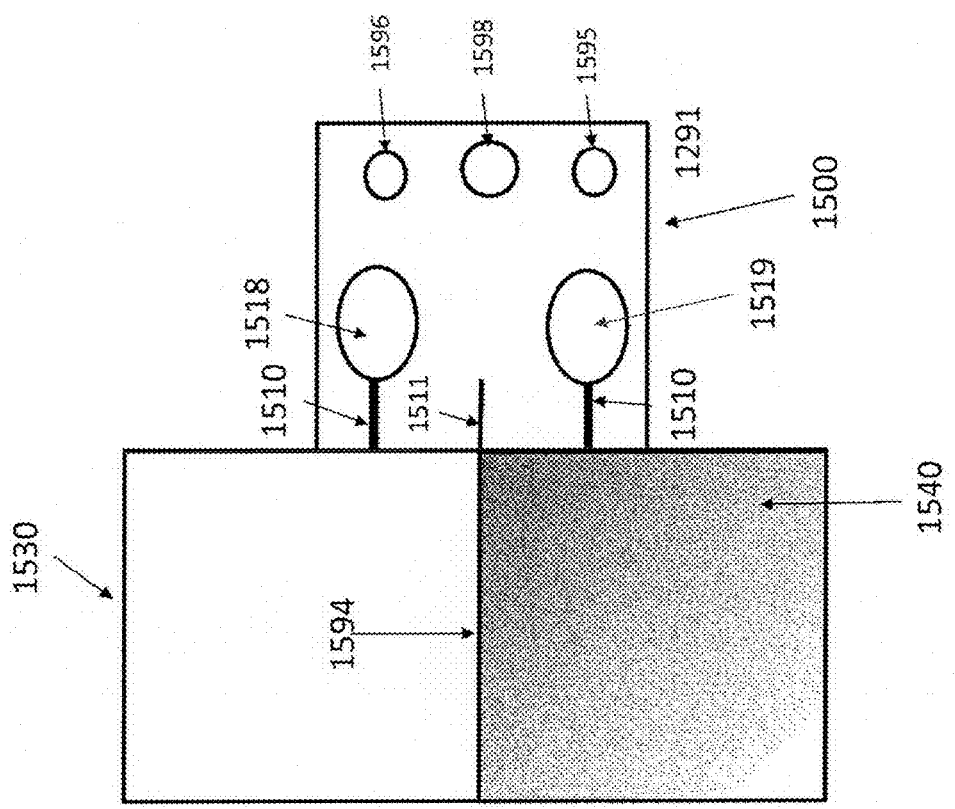
FIG. 15 shows a schematic view of an additional embodiment of the invention.

Attention is now turned to FIG. 15 which shows an embodiment of the instant invention. A liquid quality sensor 1500 includes two electric field detectors 1518 & 1519 that each includes an antenna 1510. The detector 1500 includes a centerline 1511 adapted to be placed against a waterline 1594 of a water sample 1540 in a cup 1530. A cup 1530 includes an aqueous sample 1540. This arrangement leaves one electric field detector 1518 higher than the waterline 1594, and the other 1519 lower than the waterline 1594. A local measurement of electric field on the cup 1530 is performed by each detector 1518 &1519. As the water neutralizes static electricity in the cup 1530 where the water sample 1540 is present, the lower detector 1519 should read no charge and a blue light 1595 should light up. The higher detector 1518 reads static electricity associated with the cup 1530 in a dry region of the cup 1530 a few centimeters (generally) above the waterline 1594. If static electricity is present, a green light 1596 is lit to suggest that no biological or chemical residues are present in the water sample 1540. If static electricity is absent or significantly below a predetermined threshold, the same light 1596 will show red and will warn a user that the water sample 1540 may be contaminated. The sensor 1500 may contact the cup 1530 or may be up to 20 centimeters away from the cup 1530 during measurement. Battery, on/off switch, memory, clock and other features are not shown so as to allow for easier understanding of the invention.

Ninth Embodiment

Figure 16:
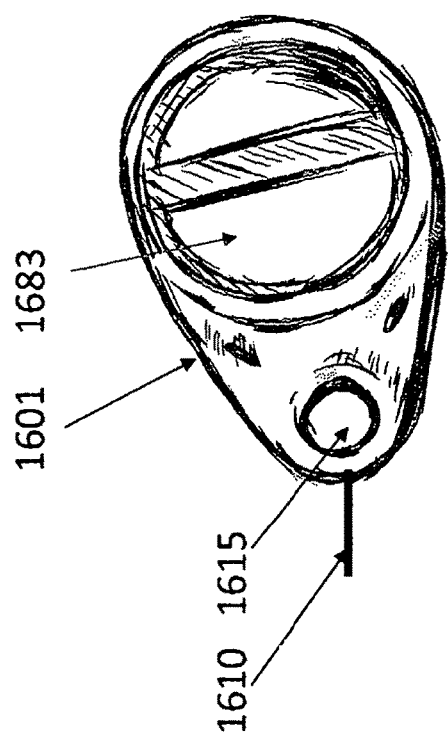
FIG. 16 shows a picture of a key fob water quality detector.
Figure 17:
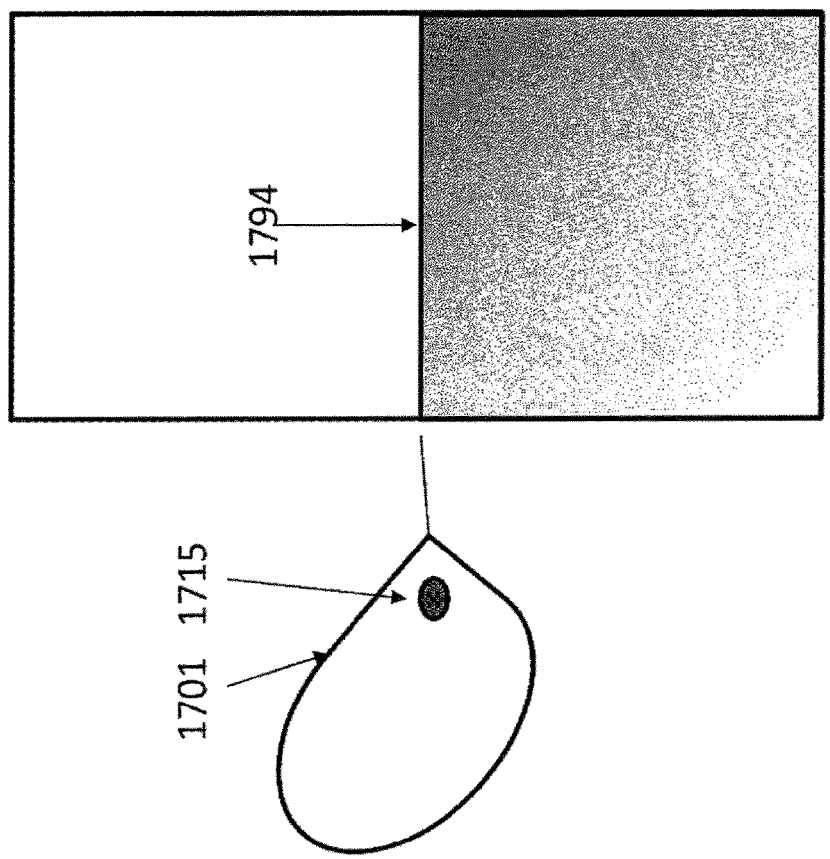
FIGS. 17-18 show pictures of the key fob in use in testing natural water sources; and, FIG. 19 shows plated sea water sample grown overnight.
Figure 18:
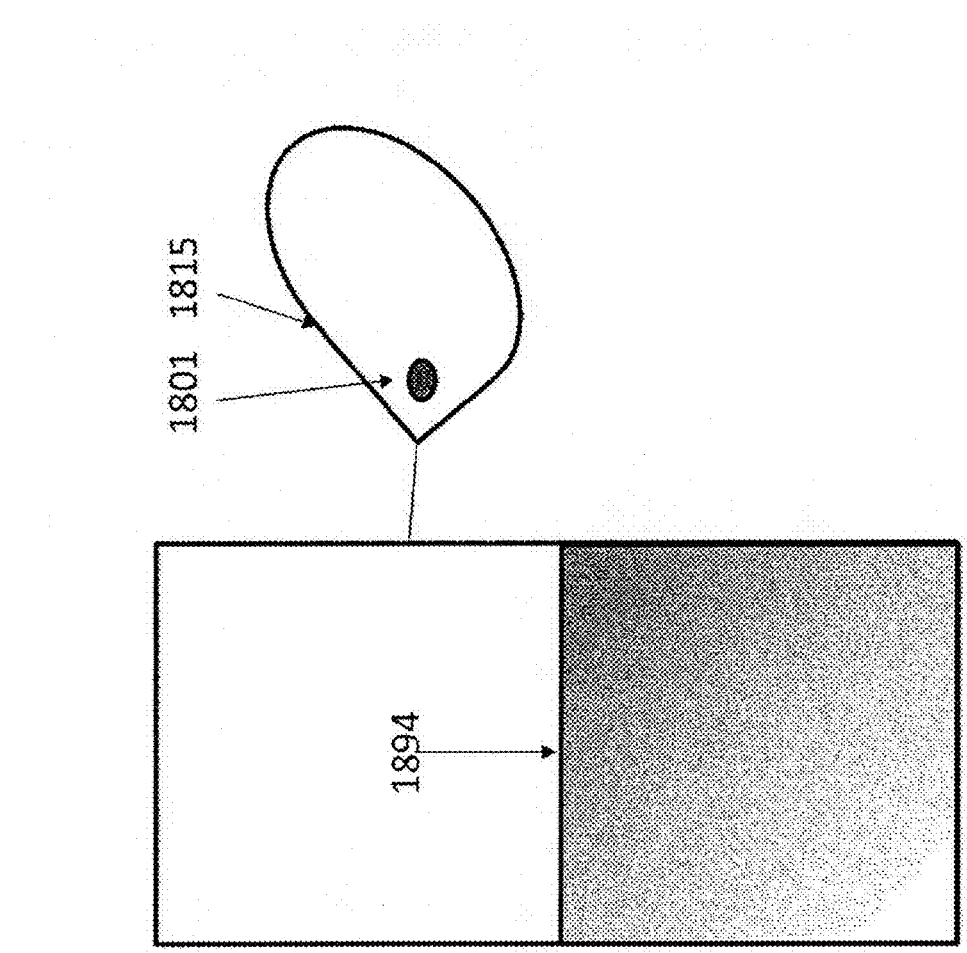

Attention is turned to FIG. 16 which shows a detection key fob 1601 that acts as a water quality detector. The key fob 1601 has a battery, an electric-field sensitive FET, and an antenna 1610. A red LED 1615 is visible and remains lit until an electrical field associated with a plastic cup or the like turns it off via an associated electronic circuit that includes a field-sensitive FET (not visible under plastic cover). The antenna 1610 is visible to the left of the LED. An on/off button 1683 is visible. The fob 1601 has been successfully deployed in field studies for testing water quality of natural water sources. FIGS. 17 & 18 show deployment of the key fob at an Israeli waterfall. FIG. 17 shows a screen grab from video of the key fob 1701 identifying clean water in a pool, as the LED 1715 turned off above the waterline 1794. FIG. 18 shows a second video screen grab, which shows contaminated water near a separate waterfall as the LED 1815 of the key fob 1801 stays lit above the waterline 1894.

Tenth Embodiment

Figure 19:
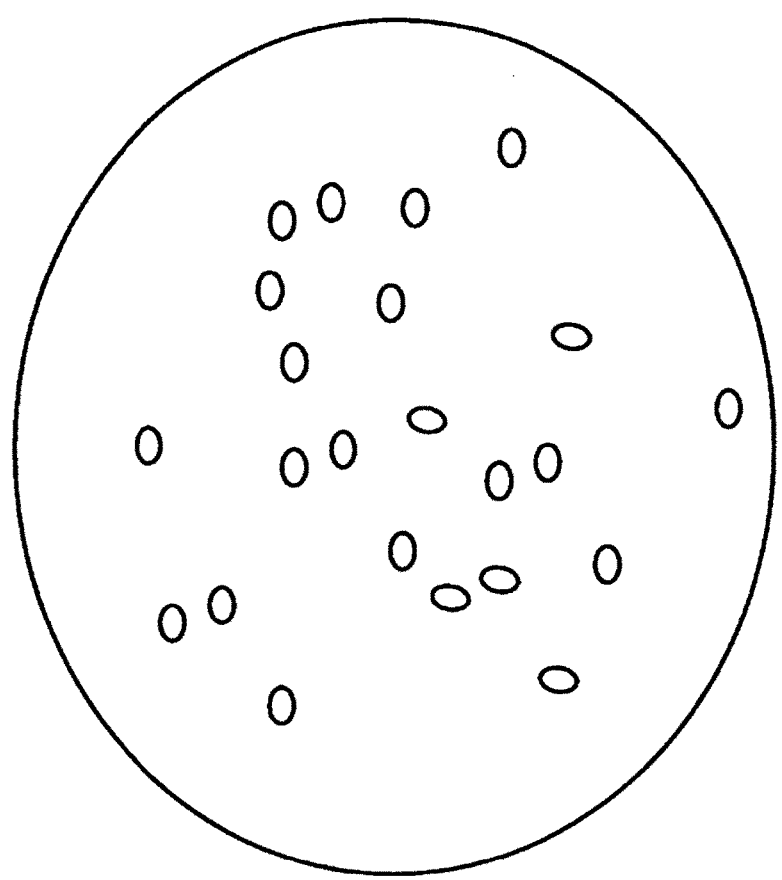

One alternative embodiment includes the possibility of swirling a liquid sample in a disposable plastic cup in the presence of a detector of electric fields, that is to swirl a cup with liquid and measure electric fields associated with the cup simultaneously, and not sequentially as per a previous embodiment. In such an arrangement, a LED associated with a detector will generally flash like a strobe light for clean water as the water is swirled in the cup in proximity to an electric field or potential detector, while a water sample that is contaminated with proteins, viruses, pathogenic bacteria or other chemical or biological residues will leave the LED lit continuously due to lower associated static charges on a cup in which swirling is performed. Such an embodiment has been successfully employed in detecting water samples with a stock protein, bovine serum albumin (BSA) versus tap water. Low bacteria concentration (~30 cfu's/mL) was detected in sea water from the Mediterranean (FIG. 19) with the instant embodiment (LED remained on for the height of the cup employed during swirling). FIG. 19 shows the results of 3 milliliters of sea water plated on a tryptic soy broth plate (Novamed, Jerusalem, Israel).

It is understood that specific chemical and/or biological detection may be performed by using appropriate antibodies, receptors, or the like attached either to a receiving element or a separate element added to a liquid sample prior to measurement of electrical fields associated with the receiving element. Thus, a plastic cup could be coated with anti-*E. coli* antibodies in order to specific identify the presence of *E. coli* in a water sample, for example.

It is expected that during the life of a patent maturing from this application, additional systems for measuring residues in liquid samples, and the scope of the term of the invention is intended to include all such new technologies a priori.

As used herein the term "about" refers to ~10%. The terms "comprises", "comprising", "includes", "including", "having" and their conjugates mean "including but not limited to". The term "consisting of" means "including and limited to". The term "consisting essentially of" means that the, method or structure may include additional ingredients, steps and/or parts, but only if the additional ingredients, steps and/or parts do not materially alter the basic and novel characteristics of the claimed composition, method or structure.

It is understood that the instant invention may be fully or partially integrated into a plurality of different devices including food safety or human diagnostic equipment. It is understood that embodiments of the instant invention could allow for measurement of many samples either sequentially or simultaneously, and the single experiments shown in the figures above is for convenience only. One obvious embodiment would be to use a compass or similar device, wherein the moving liquid or electric fields would cause a displacement of a metallic or magnetic element. The amount of displacement would be reflective of the state of the liquid and the presence or absence of any predetermined residues.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. As each number is just a symbol 20 cm could be 40 cm as well.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. The present invention could be employed for a wide variety of applications including but not limited to municipal water testing, beverage water testing, personal water testing, water safety, homeland security, beverage testing, human diagnostics, food safety, organic fluids testing, oil testing, homeland security and consumer testing of water and food products.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A device for identifying the presence of a material or class of materials in a liquid sample, including:
    a hydrophobic receiving element adapted to receive a liquid sample, wherein said receiving element and said liquid sample are adapted to generate triboelectric charge and an associated electric field by moving said liquid sample relative to said receiving element;
    an electronic circuit in non-contact proximity to said receiving element and said liquid sample, wherein said electronic circuit is adapted to measure said electric field at a plurality of positions;
    an outcome indicator in electrical communication with said electronic circuit and adapted to indicate to a user whether the concentration of the material is above or below a predetermined threshold based on the measured electric field as a function of position and,
    a source of electrical energy adapted to provide electrical energy to said electronic circuit and said indicator.

2. The device according to claim 1, wherein said receiving element is realized as a plastic cup, drinking glass, disposable shot glass, mug, bottle, pipe, sink, faucet, or tubing.

3. The device according to claim 1, wherein said proximity is realized as a distance of 0.5 to 20 centimeters.

4. The device according to claim 1, wherein said electronic circuit includes a FET element.

5. The device according to claim 1, further including a processor element adapted to receive data from said electronic circuit and control said outcome indicator.

6. The device according to claim 1, further including a GPS element for identifying location of said electronic circuit at a time of measurement of said electric field.

7. The device according to claim 1, further including a communication element adapted to send data from said processor element to a remote computing device.

8. The device according to claim 7, wherein said remote computing device is realized as a smartphone, wearable device, or mobile electronic device.

* * * * *